United States Patent [19]

Wu et al.

[11] Patent Number: 6,097,428
[45] Date of Patent: *Aug. 1, 2000

[54] METHOD AND APPARATUS FOR INSPECTING A SEMICONDUCTOR WAFER USING A DYNAMIC THRESHOLD

[75] Inventors: Wo-Tak Wu, Sudbury; Shun-Tak Wu, Maynard; Joe Danko, Franklin; Roy Foster, Stoneham, all of Mass.

[73] Assignee: Inspex, Inc.

[ * ] Notice: This patent issued on a continued prosecution application filed under 37 CFR 1.53(d), and is subject to the twenty year patent term provisions of 35 U.S.C. 154(a)(2).

[21] Appl. No.: 08/862,783

[22] Filed: May 23, 1997

[51] Int. Cl.$^7$ .............................. H04N 7/18; G06K 9/00; G01N 21/00

[52] U.S. Cl. .............................. 348/126; 348/87; 348/92; 382/145; 382/147; 356/237.4; 356/237.5

[58] Field of Search .......................... 348/86–88, 91–92, 348/125–126, 128; 382/141, 144–145, 147, 149; 356/237, 237.4, 237.5

[56] References Cited

U.S. PATENT DOCUMENTS

| | | |
|---|---|---|
| 4,667,231 | 5/1987 | Pryor ........................................ 348/128 |
| 4,772,126 | 9/1988 | Allemand et al. . |
| 5,129,009 | 7/1992 | Lebeau ...................................... 348/87 |
| 5,280,437 | 1/1994 | Corliss . |
| 5,355,212 | 10/1994 | Wells et al. .............................. 356/237 |
| 5,537,669 | 7/1996 | Evans et al. ............................. 382/141 |
| 5,625,193 | 4/1997 | Broude et al. ........................... 250/372 |
| 5,684,292 | 11/1997 | Pryor et al. .......................... 250/208.1 |

*Primary Examiner*—Vu Le
*Attorney, Agent, or Firm*—Kriegesman & Kriegesman

[57] ABSTRACT

A method and apparatus for inspecting the surface of an object such as a semiconductor wafer for contaminant particles. The apparatus includes a light source for illuminating an area on the surface of the object. A camera is positioned above the surface of the object and detects light scattered by any particles present on the surface at that area, the camera detecting light scattered from the area over a field of view, or window, which is defined by the camera, a focusing lens and the relative distance therebetween. A computer is coupled to the camera and serves to store, process, identify and/or analyze the light detected by the camera. The computer also serves to calculate a minimum light intensity threshold level which is dynamic to compensate for variances in the background light intensity of different portions of the object. The value of the threshold level is calculated for each window of the object defined by the apparatus using the equation: $T_W = \mu_W + \eta \cdot \delta_W$, where $T_W$ represents the threshold value for the particular window, $\mu_W$ represents the mean light intensity for the particular window, $\eta$ is a floating point constant value and $\delta_W$ is the light intensity standard deviation for the particular window.

4 Claims, 1 Drawing Sheet

METHOD AND APPARATUS FOR INSPECTING A SEMICONDUCTOR WAFER USING A DYNAMIC THRESHOLD

BACKGROUND OF THE INVENTION

The present invention relates generally to the inspection of semiconductor integrated circuit (IC) chips and more particularly, to a method and apparatus for inspecting a semiconductor wafer using a dynamic threshold.

Integrated circuits (ICs) are commonly manufactured through a series of processing steps. Very often more than a hundred processing steps are performed to produce a properly functioning integrated circuit chip.

A semiconductor material, commonly in the shape of a wafer, serves as the substrate for integrated circuits. Semiconductor ICs are typically manufactured as an assembly of a hundred or more chips on a single semiconductor wafer, which is then cut up to produce the individual IC chips. Typically, a wafer made of silicon is used as the integrated circuit substrate, the silicon wafer being approximately 150–200 mm in diameter and 0.5–1 mm thick. During the manufacturing process, the silicon wafer is first polished and cleaned to remove all contaminant particles situated thereon. The silicon wafer is then is treated in preparation for a series of processing steps involving a plurality of photolithographic patterns (also commonly referred to as masks). In the production of integrated circuits, microelectronic circuits are formed onto the silicon wafer through a process of layering. In the layering process, conductive and insulative layers of thin films are deposited and patterned onto the silicon wafer. Each layer is patterned by a mask designed specifically for it, the mask defining the areas within the wafer that are to be treated such as by etching or implanting.

Semiconductor fabrication technology today deals with silicon wafers which are approximately 200 mm in diameter and which feature geometries with dimensions well below 1 $\mu$m (micrometer). Due to the high complexity and level of integration of integrated circuits, the absence of contaminants on every layer of the wafer is critical in order to realize acceptable levels of product yield. However, it has been found that contaminant particles are often introduced onto the semiconductor wafer during the manufacturing process of integrated circuits. As a consequence, the presence of one contaminant particle larger than the half the width of a conductive line on the silicon wafer can result in complete failure of a semiconductor chip produced from the wafer. Such a wafer has to be discarded which thereby decreases the percentage yield per wafer and increases the overall cost of the individual chips. Therefore, a critical task facing semiconductor process engineers is to identify and, as far as possible, to eliminate sources of surface contamination on each layer of the semiconductor wafer.

Accordingly, inspection systems are well known in the art and are commonly used to detect, view, identify and correct yield limiting defects introduced in the fabrication process of integrated circuits. Wafer inspection systems typically include a light source, such as a laser, and a light sensitive imaging camera. In use, the light source is used to scan the surface of the wafer by means of illuminating particular regions of the surface of the wafer. The light sensitive imaging camera is positioned relative to the wafer to pick up scattered light for display on a viewing screen for further analysis. The imaging camera creates a visual for the viewing screen based on the number of photons which disperse from the wafer as the laser performs its scanning function. The visual could equivalently be formed by use of a non-imaging detector (e.g. a photomultiplier tube) with appropriate means of scanning for image formation. The camera will detect light scattered from any contaminant particles situated on the wafer, the intensity of the scattered light being generally proportional to the size of the particles, wherein the larger particles generally reflect more photons onto the imaging camera than smaller particles. As a consequence, larger particles will produce a brighter image and will have a greater light intensity than smaller particles.

Inspection systems of the type described above have been made commercially available by such companies as Inspex, Inc. of Billerica, Mass. For example, in U.S. Pat. No. 4,772,126 to C. D. Allemand et al, there is disclosed an apparatus and method for detecting the presence of particles on the surface of an object such the front side of a patterned semiconductor wafer. A vertically expanded, horizontally scanning, beam of light is directed onto an area on the surface of the object at a grazing angle of incidence. A video camera positioned above the surface detects light scattered from any particles which may be present on the surface, but not specularly reflected light. The surface is angularly prepositioned (rotated) relative to the incident light beam so that the diffracted light from the surface and the pattern of lines on the surface is at a minimum. The object is then moved translationally to expose another are to the incident light beam so that the entire surface of the object or selected portions thereof can be examined, an area at a time.

Inspection systems of the type described above typically establish a single, constant, minimum light intensity threshold level for the entire wafer. The minimum light intensity threshold level is established to filter out the levels of photon dispersion which fall below the threshold level from further identification and analysis. This enables the wafer inspection system to limit its detection, identification and analysis to the larger defects on the wafer which may prove to be yield limiting and accordingly filters out background noise and the relatively small particles which would typically be found not to be yield limiting. This enables the wafer inspection system to operate with increased overall inspection speed, system throughput and efficiency.

However, the establishment of a single, constant threshold level for the entire wafer has its drawbacks. Specifically, it has been found that certain conditions may cause the semiconductor wafer to appear on the imaging camera as darker in one region or lighter in another region. This regional light intensity differential could be attributed to a non-uniform or non-level layer of material being deposited on the wafer during the manufacturing process. The regional light intensity differential could also be caused by other conditions, such as if the wafer is warped or if a platform on which the wafer is placed is not perfectly level.

Due to the variances in light intensity of different regions on the wafer, a particle located in a darker region of the wafer will appear to have a relatively lower level light intensity than if that same particle were located in a lighter region. As a consequence, it has been found that large and potentially yield limiting particles which are located in darker regions of the wafer will often produce a light intensity that is below the threshold value and therefore will not be identified and analyzed. This lowers the wafer inspection system sensitivity level to the point that many large defects worthy of identification are filtered out and ignored from further analysis.

Furthermore, it has been found that small, non-yield limiting particles which are located in lighter regions of the wafer will often produce a light intensity that is above the threshold value and therefore will be detected and identified for further analysis. This creates a wafer inspection system which is oversensitive. Oversensitivity of a wafer inspection system causes many small defects which are not yield limiting to be identified and analyzed. This, in turn, decreases the speed in which the inspection system can analyze an entire wafer, thereby limiting its productivity.

SUMMARY OF THE INVENTION

It is an object of the present invention to provide a new and improved method and apparatus for inspecting a semiconductor wafer for contaminant particles.

It is another object of the present invention to provide a method and apparatus as described above which establishes a minimum, light intensity threshold level such that all particles which produce a light intensity below the threshold level are filtered out from identification and analysis.

It is yet another object of the present invention to provide a method and apparatus as described above which includes a minimum, light intensity threshold level that compensates for the variances in light intensity of different regions of the wafer.

Accordingly, there is provided an apparatus for use in inspecting the surface of an object such as a semiconductor wafer for contaminant particles, said apparatus comprising a light source for illuminating an area on the surface of the object, a camera for detecting light scattered by any particles present on the surface at that area, the intensity of the scattered light being proportional to the size of the particles, and a computer coupled to said camera for storing, processing, identifying and/or analyzing the light detected by said camera, wherein said computer calculates a minimum light intensity threshold level by which all scattered light which falls below the threshold level is filtered out from further storing, processing, identifying and/or analyzing by said computer, the threshold level for said apparatus being dynamic to compensate for variances in the background light intensity of different portions of the object.

There is also provided a method for inspecting the surface of an object such as a semiconductor wafer for contaminant particles, said method comprising the steps of illuminating an area on the surface of the object using a light source, detecting light scattered by any particles present on the surface at that area using a camera, the intensity of the scattered light being proportional to the size of the particles, said camera detecting light scattered from said area over a field of view, or window, which is defined by the camera, a focusing lens and the relative distance therebetween, and calculating a threshold level which is dynamic to compensate for variances in the background light intensity of different portions of the object, said dynamic threshold level establishing the minimum light intensity level by which all scattered light which falls below the threshold level light intensity is filtered out from further storing, processing, identification and/or analysis.

Various other features and advantages will appear from the description to follow. In the description, reference is made to the accompanying drawings which form a part thereof, and in which is shown by way of illustration, a specific embodiment for practicing the invention. The embodiment will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

BRIEF DESCRIPTION OF THE DRAWINGS

In the drawings wherein like reference numerals represent like parts.

DETAILED DESCRIPTION OF THE PREFERRED EMBODIMENT

Figure 1:
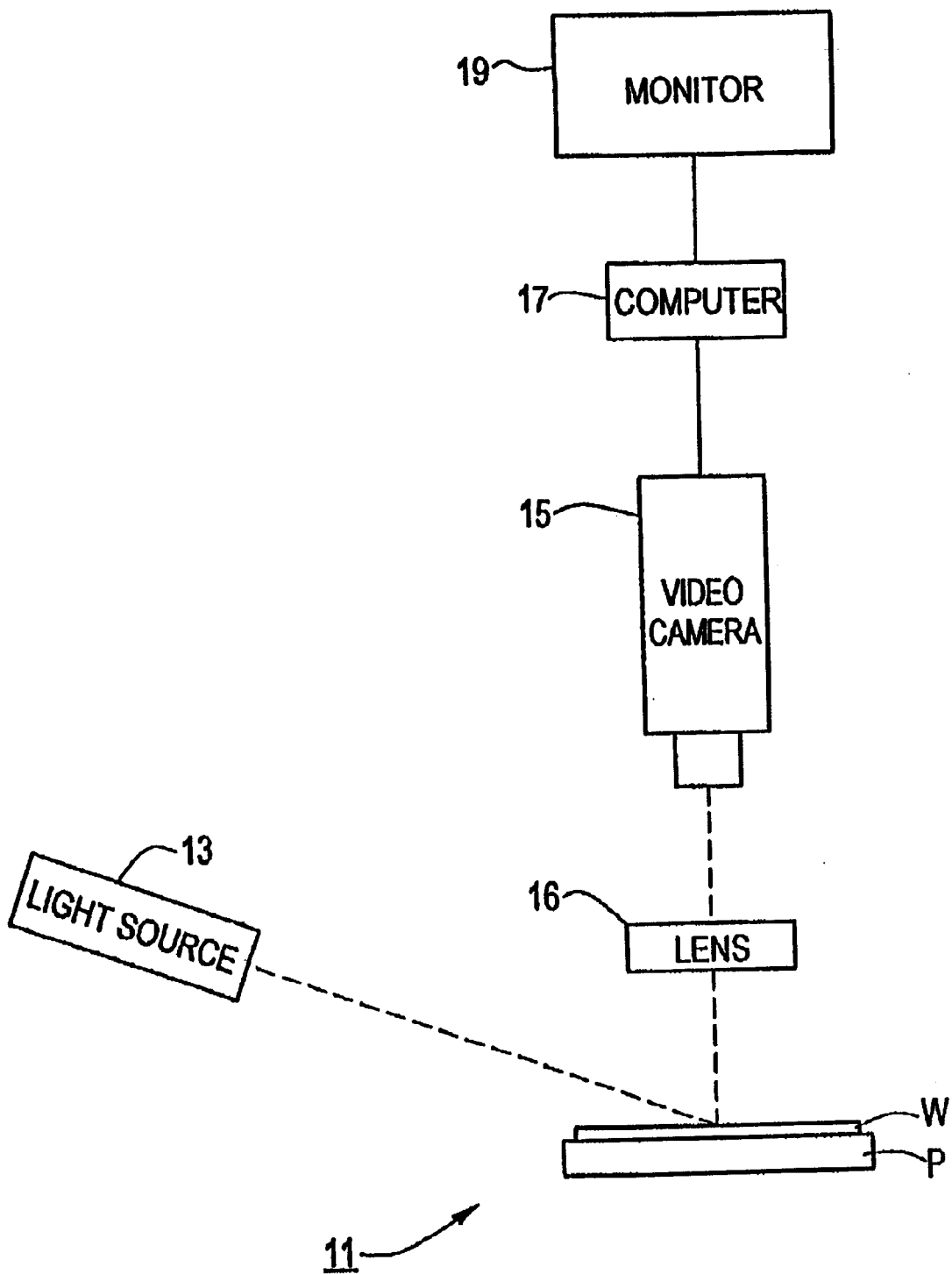
FIG. 1 is a schematic representation of an embodiment of an apparatus constructed according to the teachings of the present invention for detecting the presence of particles on the surface of a semiconductor wafer.

The present invention is directed to a method and apparatus for inspecting a semiconductor wafer using a dynamic threshold.

In accordance with the invention, there is provided an apparatus for inspecting a semiconductor wafer W using a dynamic threshold, the apparatus being identified by reference numeral 11.

Referring now to FIG. 1, apparatus 11 comprises a light source 13 for illuminating wafer W for inspection, a video camera 15 for detecting light scattered off of wafer W from light source 13, a lens 16 for focusing scattered light onto camera 15 and a computer 17 for storing, processing, identifying and/or analyzing the light detected by video camera 15.

Light source 13 is preferably a laser which produces a high intensity monochromatic beam of light that is used to scan wafer W for contaminant particles situated thereon, wafer W being shown supported by a platform P. Specifically, light source 13 produces a beam of light which is directed onto the top surface of a section of wafer W, thereby illuminating said section.

Video camera 15 is preferably a high light sensitive charge coupled device (CCD) camera and is positioned above the surface of semiconductor wafer W so as detect light scattered off of wafer W from light source 13. Light which is scattered by any contaminant particles present on the section of wafer W illuminated by light source 13 is focused by lens 16 onto video camera 15 for detection. The section of wafer W which is detected by video camera 15 is limited to a field of view defined by camera 15, lens 16 and the relative distance therebetween. This field of view is often referred to as the window, or image, size for apparatus 11. The window size can vary but it typically is in the range from approximately 2 mm by 2 mm to approximately 10 mm by 10 mm for high speed applications.

Camera 15 is connected to computer 17. Computer 17 serves to store, process, identify and/or analyze the particular light intensity information which was detected by camera 15. Computer 17 is of the type commonly used in semiconductor wafer inspection systems. Specifically, computer 17 is of the type which is programmed to calculate the mean ($\mu$) and standard deviation ($\delta$) of the light intensity within each window defined by apparatus 11.

A display monitor 19 is coupled to computer 17. The light intensities within each window which are detected by camera 15 can be processed by computer 17 and displayed on monitor 19 to provide an image of the portion of wafer W illuminated by light source 13. Monitor 19 is of the type commonly used in semiconductor wafer inspection systems.

In order to limit the detection, identification and examination of background noise and non-yield limiting particles, computer 17 is programmed to implement a minimum light intensity threshold level. The minimum light intensity threshold level is established to filter out the amounts of photon dispersion which fall below the threshold level from further identification and analysis. As such, the minimum light intensity threshold level determines the sensitivity of the apparatus 11.

For the present invention, computer 17 is programmed to implement a minimum light intensity threshold level T which is dynamic. Computer 17 utilizes dynamic threshold T because certain conditions may cause wafer W to appear on imaging camera 15 as darker in one region or lighter in another region. The variance in light intensity of different regions on wafer W can cause large and potentially yield limiting particles located in the darker regions of wafer W to be filtered from identification and analysis. In addition, the variance in light intensity of different regions on wafer W can cause small, non-yield limiting particles located in lighter regions of wafer to be identified and analyzed, thereby limiting productivity.

In use, computer 17 establishes dynamic threshold T using the following two-step method, the two-step method including a setup mode and a production mode. It should be noted that both steps of the two-step method can be accomplished by computer 17 using a computer program.

In the setup mode, light source 13 illuminates wafer W and camera 15 detects the scattered light in various windows on wafer W. Upon detection of the scattered light by camera 15, computer 17 determines the mean ($\mu$) and standard deviation ($\delta$) of the light intensity for each of the windows defined by apparatus 11. Computer 17 then determines which window of wafer W has the highest standard deviation $\delta$.

The threshold T for the particular window which has the highest standard deviation $\delta$ is then adjusted to just above the noise level. Specifically, the threshold T is raised if apparatus 11 detects too many false counts (non-particles) and the threshold T is lowered if apparatus 11 detects no or too few particles that are shown as being present on the wafer. Once the ideal threshold is established by the user, the floating point constant n for apparatus 11 is calculated using the following equation:

$$n = (T - \mu)/\delta,$$

where T is the ideal threshold level for the particular window, $\mu$ is the mean light intensity for the particular window, and $\delta$ is the standard deviation for the particular window. The calculation of floating point constant n completes the setup mode.

In the production mode, light source 13 illuminates wafer W and camera 15 detects the scattered light for each window on wafer W. Upon detection of the scattered light by camera 15, computer 17 determines the mean ($\mu_W$) and standard deviation ($\delta_W$) of the light intensity for each window defined by apparatus 11. Computer 17 then calculates the dynamic threshold $T_W$ for each window using the following equation:

$T_W = \mu_W + n \cdot \delta_W$, where $T_W$ is the dynamic threshold for the particular window, $\mu_W$ is the mean light intensity for the particular window, n is the floating point constant calculated in the setup mode and $\delta_W$ is the standard deviation for the particular window.

It should be noted that establishing a dynamic threshold which recalculates the threshold for each window on wafer W significantly corrects the problems that result from using a constant threshold value for the entire wafer which were noted above.

The embodiment shown in the present invention is intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. An apparatus for use in inspecting the surface of an object for contaminant particles, said apparatus comprising:
   (a). a light source for illuminating an area on the surface of the object,
   (b). a camera for detecting light scattered by any particles present on the surface at that area, the intensity of the scattered light being proportional to the size of the particles,
   (c). a lens for focusing said scattered light onto said camera, said camera detecting light scattered from the area on the surface of the object over a field of view, or window, which is defined by said camera, said lens and the relative distance therebetween, and
   (d). a computer coupled to said camera for storing, processing, identifying and/or analyzing the light detected by said camera, wherein said computer calculates a minimum light intensity threshold level for each window of the object defined by said apparatus based on light intensity characteristics of the particular window by which all scattered light which falls below the threshold level is filtered out from further storing, processing, identifying and/or analyzing by said computer, herein the value of the theseshold level for each window of the object defined by said apparatus is calculated using the equation:

$$T_W = \mu_W + \eta \delta_W$$

where $T_W$ represents the threshold value for the particular window, $\mu_W$ resents the mean light intensity for the particular window, $\eta$ is a floating point constant value and $\delta_W$ is the light intensity standard deviation for the pagicular window.

2. The apparatus as claimed in claim 1 further comprising a display monitor coupled to said computer for displaying the information which is stored, processed, identified and/or analyzed by said computer.

3. A method for inspecting the surface of an object for contaminant particles, said method comprising the steps of:
   (a). illuminating an area on the surface of the object using a light source,
   (b). detecting light scattered by any particles present on the surface at that area using a camera, the intensity of the scattered light being proportional to the size of the particles, the camera detecting light scattered from the area over a field of view, or window, which is defined by the camera, a focusing lens and the relative distance therebetween, and
   (c). calculating a threshold level which is dynamic to compensate for variances in the background light intensity of different portions of the object, said dynamic threshold level establishing a minimum light intensity threshold level for each window of the object based on light intensity characteristics of the particular window by which all scattered light which falls below the minimum light intensity threshold level is filtered out from further storing, processing, identification and/or analysis, wherein the value of the minimum light intensity threshold level for each window of the object is accomplished using the formula:

$$T_w = \mu_w + \eta \, \delta_w$$

where $T_w$ represents the threshold value for the particular window, $\mu_w$ represents the mean light intensity for the particular window, $\eta$ is a floating point constant value and $\delta_w$ is the light intensity standard deviation for the particular window.

4. The method for inspecting the surface of an object as claimed in claim 3 wherein said step of calculating the minimum light intensity threshold level for each window of the object is accomplished by a computer coupled to said camera.

* * * * *